(12) United States Patent
Matzinger et al.

(10) Patent No.: US 6,884,592 B2
(45) Date of Patent: Apr. 26, 2005

(54) DEVICES FOR ANALYTE CONCENTRATION DETERMINATION AND METHODS OF MANUFACTURING AND USING THE SAME

(75) Inventors: David Matzinger, Menlo Park, CA (US); Khalid R. Quraishi, Sunnyvale, CA (US); Yeung Siu Yu, Pleasanton, CA (US)

(73) Assignee: LifeScan, Inc., Milpitas, CA (US)

( * ) Notice: Subject to any disclaimer, the term of this patent is extended or adjusted under 35 U.S.C. 154(b) by 289 days.

(21) Appl. No.: 09/946,215

(22) Filed: Sep. 5, 2001

(65) Prior Publication Data

US 2003/0044854 A1 Mar. 6, 2003

(51) Int. Cl.[7] .............................................. G01N 33/53
(52) U.S. Cl. ........................ 435/7.1; 422/56; 422/57; 422/58; 422/60; 435/7.92; 435/7.93; 435/7.94; 435/970; 436/501; 436/514; 436/518; 436/524; 436/525; 436/528; 436/808; 436/810
(58) Field of Search ................................. 435/7.1, 7.92, 435/7.93, 7.94, 970; 436/501, 514, 518, 528, 525, 808, 810; 422/56, 57, 58, 60

(56) References Cited

U.S. PATENT DOCUMENTS

| | | | |
|---|---|---|---|
| 4,587,099 A | | 5/1986 | Rothe et al. |
| 4,839,296 A | | 6/1989 | Kennedy et al. |
| 5,179,005 A | | 1/1993 | Phillips et al. |
| 5,447,689 A | * | 9/1995 | Gibboni et al. ................ 422/56 |
| 5,515,170 A | | 5/1996 | Matzinger et al. |
| 5,563,042 A | | 10/1996 | Phillips et al. |
| 5,573,921 A | * | 11/1996 | Behnke et al. ............. 435/7.92 |
| 5,605,837 A | | 2/1997 | Karimi et al. |
| 5,620,863 A | | 4/1997 | Tomasco et al. |
| 5,652,148 A | * | 7/1997 | Doshi et al. ................ 436/178 |
| 5,753,452 A | | 5/1998 | Smith |
| 5,789,255 A | | 8/1998 | Yu |
| 5,843,691 A | | 12/1998 | Douglas et al. |
| 5,968,836 A | | 10/1999 | Matzinger et al. |
| 5,972,294 A | | 10/1999 | Smith et al. |
| 6,168,957 B1 | | 1/2001 | Matzinger et al. |
| 2001/0051352 A1 | * | 12/2001 | Krantz et al. .................. 435/14 |
| 2003/0203498 A1 | * | 10/2003 | Neel et al. ..................... 436/95 |

FOREIGN PATENT DOCUMENTS

| | | | |
|---|---|---|---|
| EP | 0 574 134 | | 12/1993 |
| EP | 0 974 840 | | 1/2000 |
| WO | WO 9303842 | * | 3/1993 |
| WO | WO 99 32883 | | 7/1999 |

* cited by examiner

Primary Examiner—Bao-Thuy L. Nguyen
(74) Attorney, Agent, or Firm—Carol M. LaSalle; Susan C. Tall; Bozicevic, Field & Francis LLP

(57) ABSTRACT

Test strips for determining the concentration of at least one analyte, e.g., glucose, in a physiological sample and methods for their manufacture and use and are provided. The subject test strips include a transfer element for facilitating the transfer of sample to a reaction area of the test strip. In certain embodiments, the transfer element, typically porous, has a first area and a second area, and in certain embodiments the two areas have different thicknesses. In other embodiments, the transfer element is non-porous and is configured to transfer sample by wicking it between the transfer element and the reaction area of the test strip. In the subject methods, the transport element facilitates transfers of a sample to a reaction area of the test strip. The subject test strips and methods find use in a variety of different applications, particularly in the determination of glucose concentrations.

17 Claims, 7 Drawing Sheets

DEVICES FOR ANALYTE CONCENTRATION DETERMINATION AND METHODS OF MANUFACTURING AND USING THE SAME

FIELD OF THE INVENTION

The field of this invention is analyte concentration determination, particularly physiological sample concentration determination and more particularly glucose concentration determination.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte concentration determination, a variety of analyte concentration determination protocols and devices for both clinical and home testing have been developed. For example, various calorimetric or photometric test strips are known that contain one or more testing reagents associated with a testing or reaction area, where the reagent(s) turns a different shade of color depending on the concentration of a particular analyte, such as glucose in a blood sample that has been applied to the reaction area of the test strip. The blood glucose concentration is measured by either comparing the color to a color chart or by inserting the strip into a meter such as a reflectance photometer or the like, which automatically determines the concentration from the change in color caused by the reaction between the testing reagent(s) and the analyte. Typically, a test strip, and more particularly a colorimetric or photometric test strip includes (1) a substrate including one or more reaction or testing reagents, i.e., a reaction area, (2) a support layer which provides structural support to the strip and oftentimes includes an aperture therethrough for viewing the substrate, and (3) a material that assists in the transfer of sample to the reaction area, i.e., a transferring or filtering material or structure.

However, to determine the concentration of an analyte in a physiological sample, a physiological sample must first be obtained and brought into contact with a reaction area of the test strip so that the physiological sample, and more particularly the analyte of interest or derivative thereof, may react with the testing reagent(s) associated with the reaction area. In order to obtain an accurate measurement of the particular analyte(s) of interest, a minimum sample volume must be applied to the reaction area. It can be appreciated that inaccurate measurements can result in serious and even life-threatening consequences for those whose lives depend on frequent monitoring of an analyte in their body, for example glucose monitoring for diabetics.

Figure 5A:
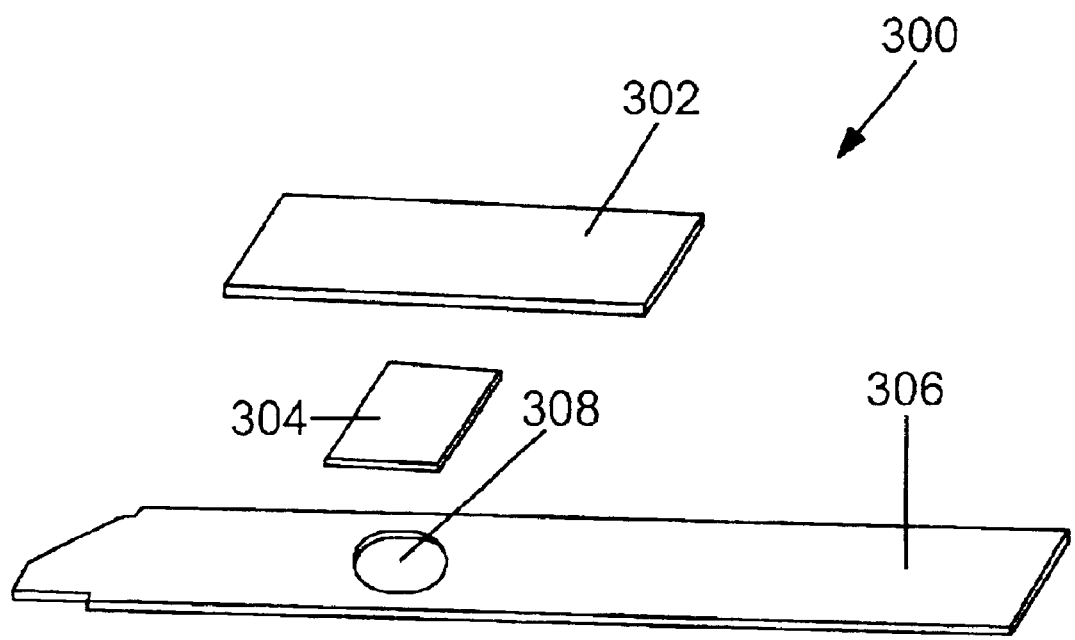
Figure 5B:
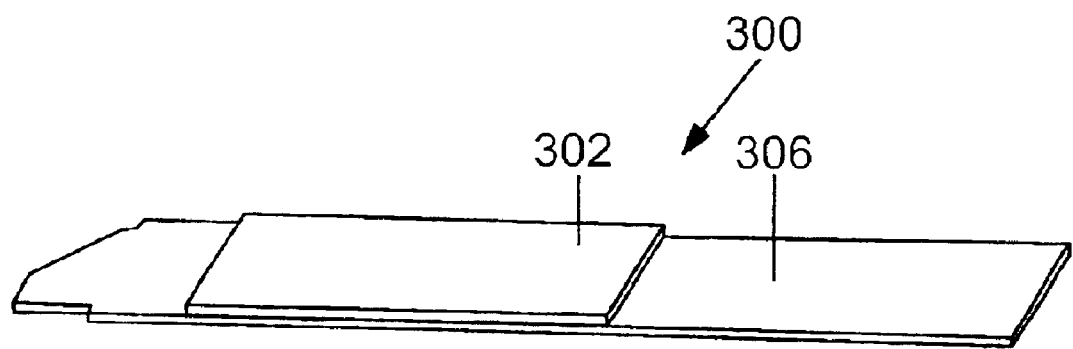

FIGS. 5A and 5B show views of an exemplary, conventional test strip. FIG. 5A shows an exploded view of a conventional test strip configuration and FIG. 5B shows the configured test strip of FIG. 5A. Test strip 300 includes, as described above, a support layer 306 having an aperture 308 therethrough, a reaction area 304 and a transfer material 302 associated with the reaction area 304, i.e., lying directly above or on top of the reaction area 304. As can be seen, the fluid transfer material 302 is a unidimensional piece of material. That is, the shape and the dimensions such as the thickness and width of the transfer material 302 are constant throughout the entire structure. Typically, the transfer material is generally fabricated to have a thickness of about 0.020 to 0.030 inches, a width of about 0.20 to 0.30 inches and a length of about 0.90 to 1.10 inches.

Typically, a patient obtains physiological sample such as blood, blood fractions or interstitial fluids, from a finger or arm puncture site, where the volume of sample obtained from such a puncture may vary considerably depending on the particular patient, the sampling site and the like. Sample is applied first to the transfer material or structure in communication with the reaction area of the test strip and then a portion of the sample is then filtered through to the reaction area. The transfer material is usually configured and sized to retain or hold excess sample so that the excess sample does not contaminate other portions of the test strip or contaminate portions of an automatic device into which the test strip is inserted for automatically performing the testing processes. Such contamination may cause false or inaccurate results.

Thus, this transfer material assists in sample collection and helps to dissipate or spread the sample evenly over the reaction area, retain excess sample and may further serve to filter our or exclude unwanted components in the sample before they reach the reaction area. Although this material plays an important role in sample transfer to the reaction area, it has certain disadvantages associated with it. First and foremost, to transfer sample through the material to the reaction area, the portion of the material over the reaction area must first reach saturation, where the volume of sample needed to saturate the material is much greater than what is required by the reaction area to perform an accurate test. Usually, a sample volume of about 7 to 50 microliters and more usually about 7 to 10 microliters is needed to saturate the filter or transfer material of currently configured test strips, however only 1 to 3 microliters is actually needed at the reaction area. Thus, it will be apparent that this transfer material determines the volume of sample that is required from the patient, not the actual volume needed by the reaction area to perform an accurate test.

This rather larger volume of sample needed to saturate this material is often difficult to obtain from a patient. For example, obtaining this volume may require the use of a large diameter needle and/or deeper penetration into the skin. Even if a large diameter needle is used and/or a needle has been penetrated deep into the skin, oftentimes, a first puncture produces insufficient volume for the particular test being performed and thus the skin must be punctured again until a sufficient volume is ultimately obtained. These factors can increase discomfort and pain felt by the patient, and may be extremely difficult to achieve for those individuals whose capillary blood does not readily express. As this sampling process may require repeating frequently within a single day, for many patients, the pain associated with sample collection quickly becomes less tolerable or intolerable all together.

Furthermore, conventional test strip configurations using a material to transfer sample to the test strip require the sample be applied directly to the center of the transfer material or top of the test strip. In other words, the patient must either (1) hold the test strip with the transfer material facing up and turn a finger toward the material so that the sample drop expressed therefrom goes downward onto the strip or, alternatively, (2) position the strip, transfer material side down, onto a finger with a sample drop facing upward. Either way, the patient's view of the material is obscured, blocking the view of how much sample has been applied to the material and thus how much more is needed until the material is saturated. This disadvantage often results in patients applying a volume of sample greater than that which is required, further contributing to the pain and discomfort associated with sample collection.

As such, there is continued interest in the development of new devices and methods for use in the determination of analyte concentrations in a physiological sample. Of particular interest would be the development of such devices, and methods of use thereof, that require minimal sampling volumes, i.e., the transfer material possesses small void volumes, enable the dissipation or spread of the sample evenly over the reaction area, retain excess sample, filter unwanted components in the sample before they reach the reaction area, are easy to use and easy to manufacture.

Relevant Literature

References of interest include: U.S. Pat. Nos. 5,515,170 and 6,168,957 B1.

SUMMARY OF THE INVENTION

Test strips for determining the concentration of at least one analyte, e.g., glucose, in a physiological sample and methods for their manufacture and use and are provided. The subject test strips include a transfer element for facilitating the transfer of sample to a reaction area of the test strip. In certain embodiments, the transfer element, typically porous, has a first area and a second area, and in certain embodiments the two areas have different thicknesses. In other embodiments, the transfer element is non-porous and is configured to transfer sample by wicking it between the transfer element and the reaction area of the test strip. In the subject methods, the transport element facilitates transfers of a sample to a reaction area of the test strip. The subject test strips and methods find use in a variety of different applications, particularly in the determination of glucose concentrations.

BRIEF DESCRIPTIONS OF THE DRAWINGS

Figure 1A:
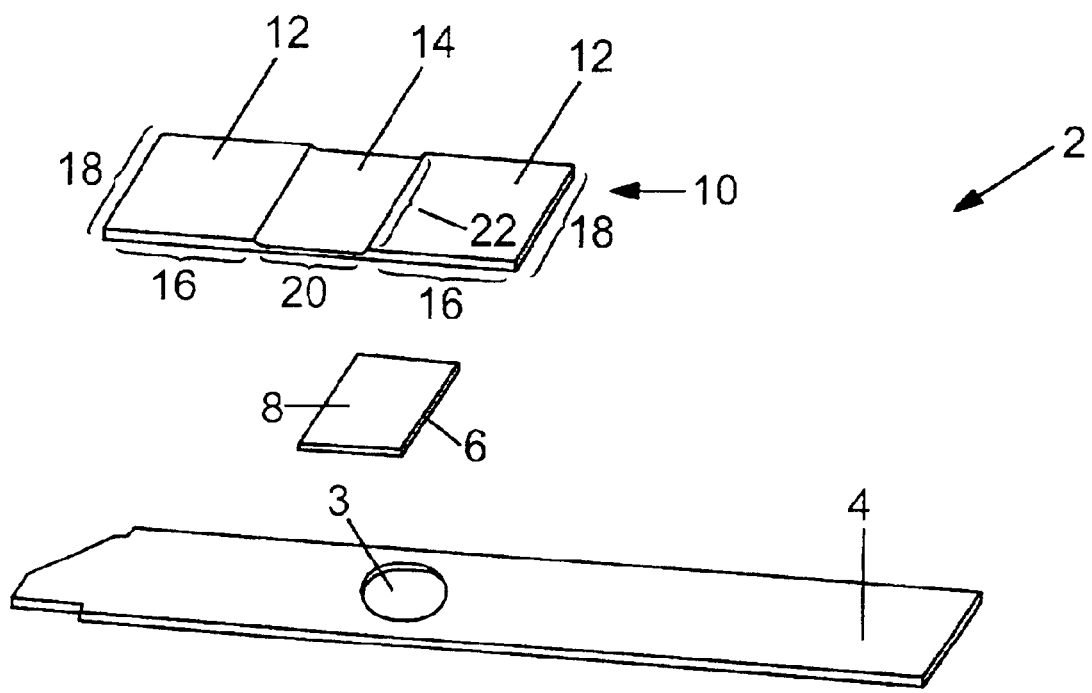
Figure 1B:
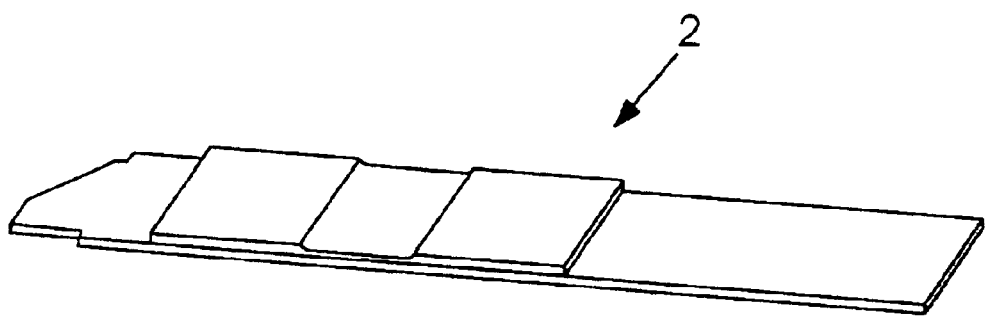
Figure 1C:
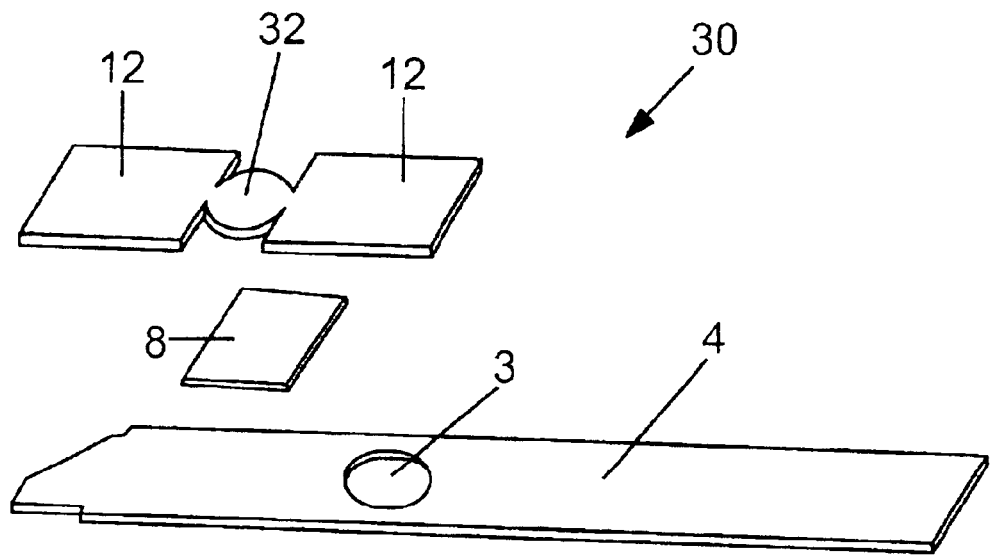
Figure 1D:
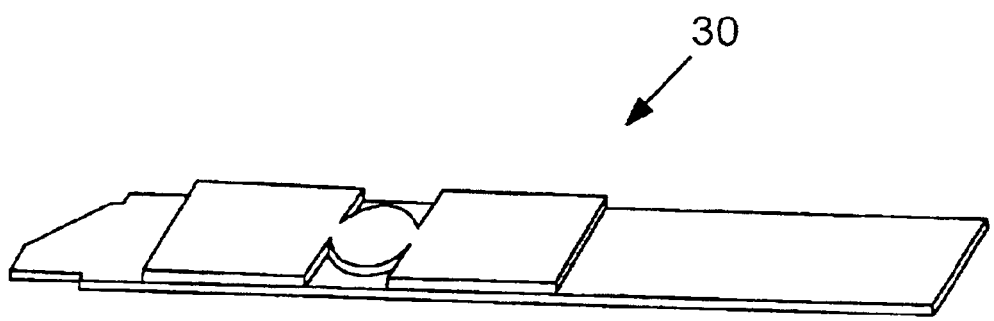
Figure 1E:
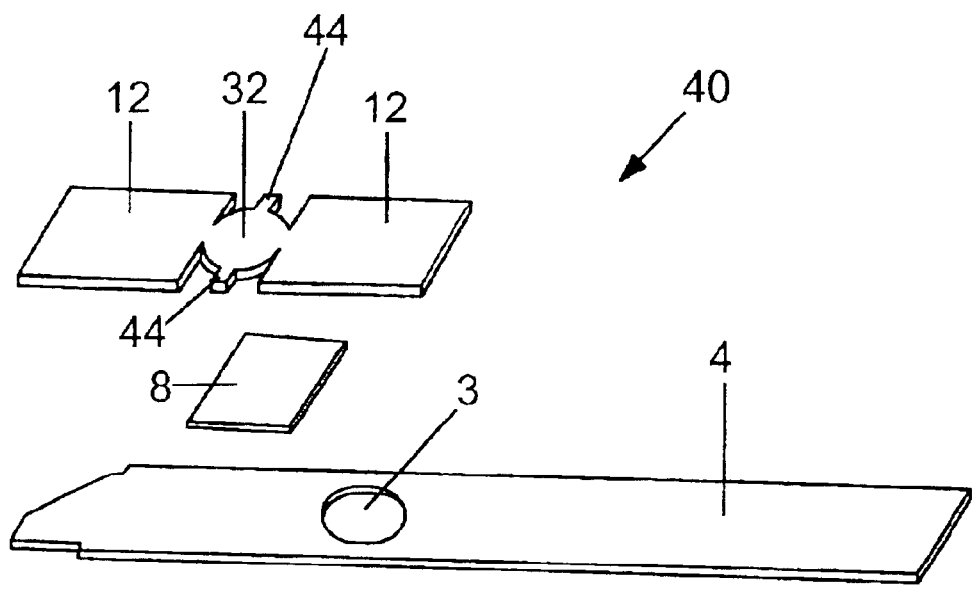
Figure 1F:
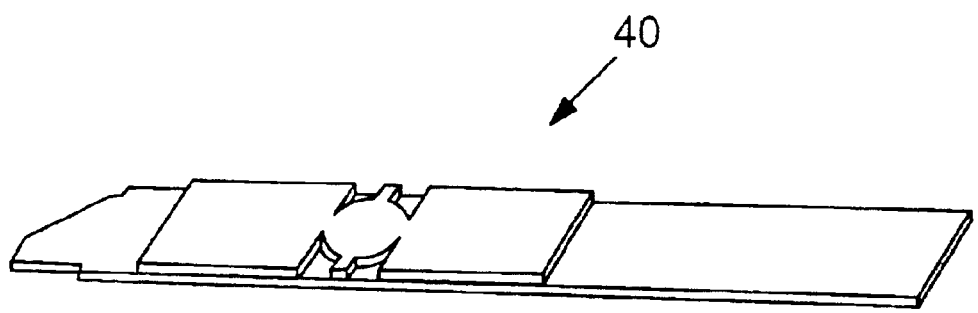
Figure 1G:
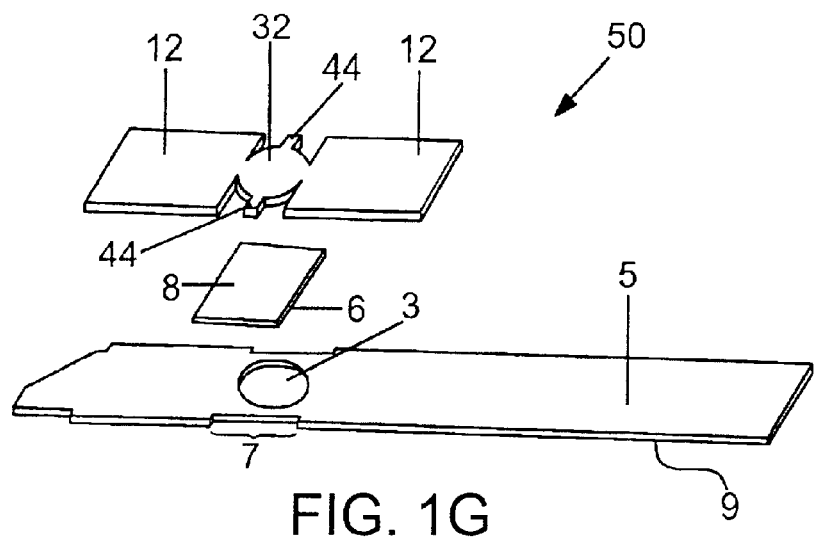

FIGS. 1A-1D are exemplary embodiments of the test strips of the subject invention having a porous transport element with at least a first area and a second area having different thicknesses. FIG. 1A shows an exploded view of embodiment where the transport element has a substantially rectangular second area and FIG. 1B shows the configured test strip of FIG. 1A. FIG. 1C shows an exploded view of an embodiment where the transport element has a substantially circular second area. FIG. 1D shows the configured test strip of FIG. 1C. FIG. 1E shows an exploded view of an embodiment where the transport element has two lateral extensions operatively associated with it. FIG. 1F shows the configured test strip of FIG. 1E. FIG. 1G shows an exploded view of an embodiment where the support layer of the test strip has notches therein.

Figure 2A:
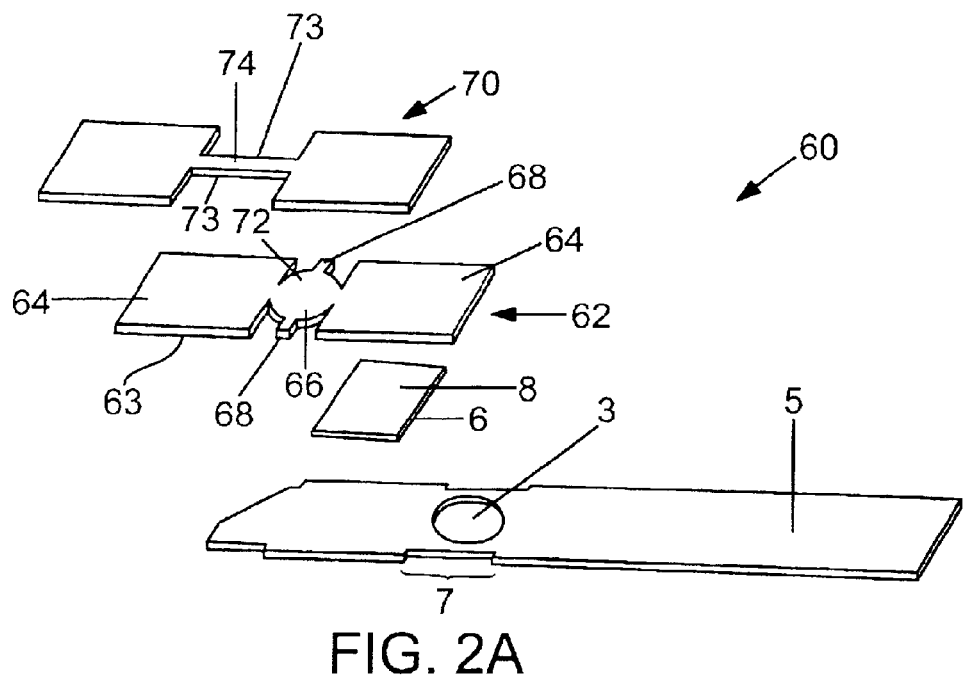
Figure 2B:
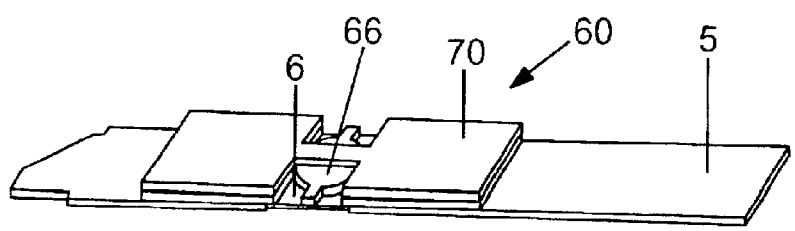
Figure 2C:
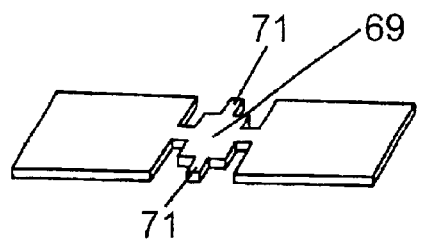

FIGS. 2A-2C are embodiments of the subject invention having a non-porous transport element. FIG. 2A shows an exploded view of an embodiment having a sample confinement element. FIG. 2B shows the configured test strip of FIG. 2A. FIG. 2C shows an embodiment of a non-porous transport element having a substantially rectangular shaped second area and lateral extensions.

Figure 3A:
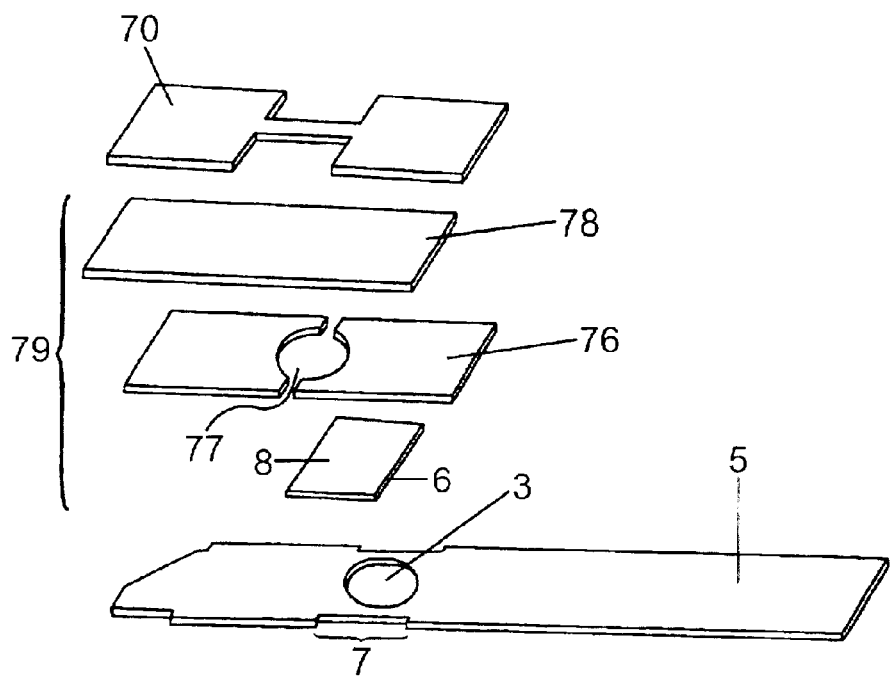
Figure 3B:
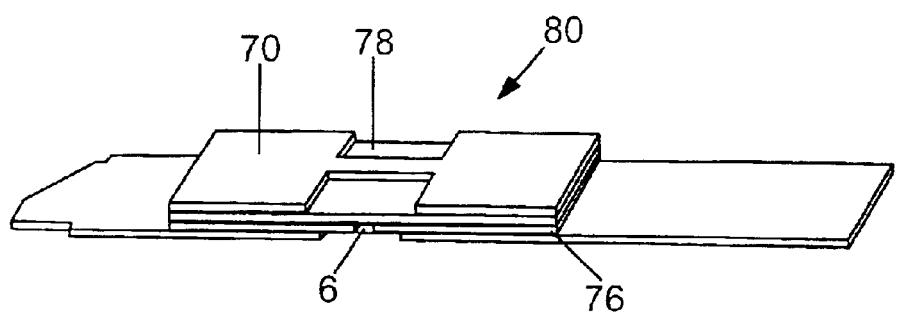

FIG. 3A shows an exploded view of another embodiment of the subject test strip having a spacer layer, a non-porous layer and a sample confinement layer. FIG. 3B shows the configured test strip of FIG. 3A.

Figure 4A:
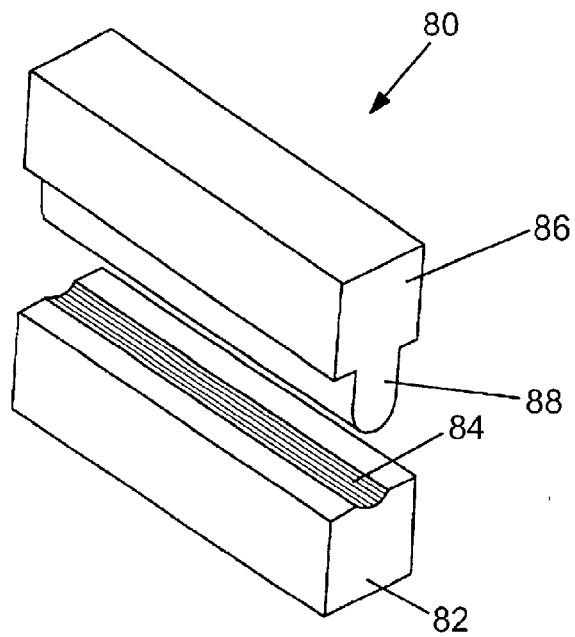
Figure 4B:
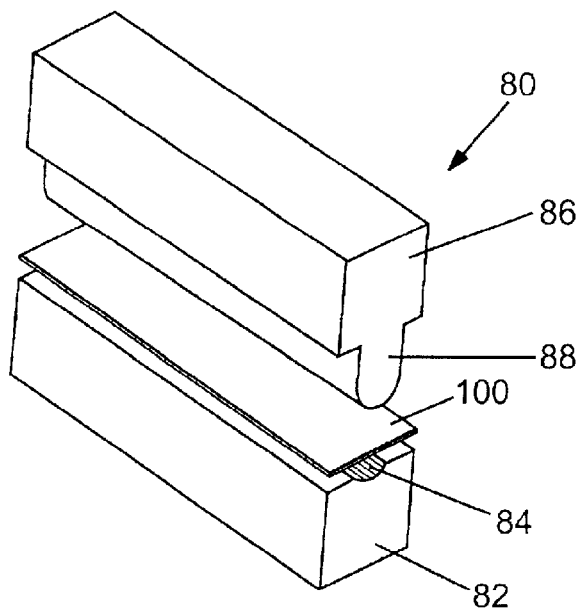
Figure 4C:
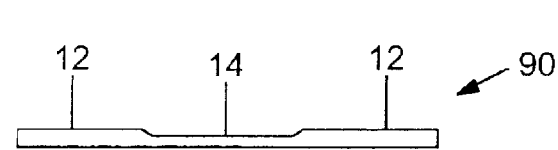
Figure 4D:
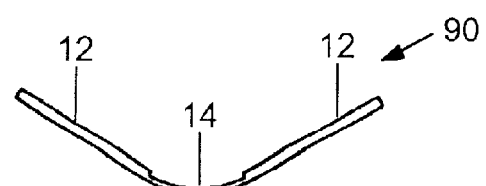

FIG. 4A shows an exemplary embodiment of a compression molding assembly for use in manufacturing the test strips of the subject invention having areas of differing thicknesses. FIG. 4B shows the assembly of FIG. 4A having a precursor transport element material positioned therein. FIG. 4C shows a side view of an exemplary transport element that has been formed by the subject methods in its unfolded state. FIG. 4D shows a side view of the formed transport element of FIG. 4C in its pressed state.

FIG. 5A shows an exploded view of embodiment of a conventional test strip and FIG. 5B shows the configured test strip of FIG. 5A.

DETAILED DESCRIPTION OF THE INVENTION

Test strips for determining the concentration of at least one analyte, e.g., glucose, in a physiological sample and methods for their manufacture and use and are provided. The subject test strips include a transfer element for facilitating the transfer of sample to a reaction area of the test strip. In certain embodiments, the transfer element, typically porous, has a first area and a second area, and in certain embodiments the two areas have different thicknesses. In other embodiments, the transfer element is non-porous and is configured to transfer sample by wicking it between the transfer element and the reaction area of the test strip. In the subject methods, the transport element facilitates transfers of a sample to a reaction area of the test strip. The subject test strips and methods find use in a variety of different applications, particularly in the determination of glucose concentrations. In further describing the subject invention, the subject devices will be described first, followed by a review of the subject methods of manufacture and methods of use for practicing the subject devices.

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. Thus, for example, reference to "a test strip" includes a plurality of such test strips and reference to "the device" includes reference to one or more devices and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Devices

As summarized above, the subject invention provides test strips for determining the concentration of an analyte in a physiological sample, where the test strips are configured to require only a minimal volume of sample. The subject test strips find use in the determination of a wide variety of different analyte concentrations, where representative analytes include, but are not limited to, glucose, cholesterol, lactate, alcohol, and the like. In many embodiments of the subject devices, the test strips are used to determine the glucose concentration in a physiological sample, e.g., interstitial fluid, blood, blood fractions, constituents thereof, and the like.

While it is to be understood that a variety of different types of test strips may be suitable for use with the present invention, e.g., colorimetric or photometric (used herein interchangeably) and electrochemical, the subject invention will be described herein in reference to a photometric assay system, where such description is by way of example and not limitation.

Generally, the subject test strips include a substrate, e.g., a porous membrane or the like, that incorporates one or more testing reagents, where the testing reagents react with components or analytes in a physiological sample applied thereto. This porous membrane with associated reagents is referred to herein as the reaction area or zone of the test strip. The membrane is typically associated with a backing or support layer and the test strip may also include a fluid transport element, typically a porous transfer element, attached to one side of the membrane, where a support layer is typically attached to the other side of the membrane (see FIGS. 1A and 1B for an exemplary embodiment of such a test strip). An aperture through the support layer provides a view of the membrane. In those devices having a porous transport element, physiological sample is applied to the transport element and at least a portion of the applied sample, i.e., the volume necessary to make an accurate measurement, travels through the transport element to the reaction area. In other embodiments of the subject test strips, a non-porous transport element or layer is present instead of the porous transport element, where physiological sample is applied between the non-porous layer and the porous membrane. The components of the test strips and various embodiments thereof will now be described in more detail.

The Porous Membrane

The membrane of the test strip may be of a uniform composition or may be a coated substrate. It includes a sample side to which the transport medium or other material layer, as will be described below, is attached, and a testing side where a color change is observed, from which the detection and/or concentration of an analyte is determined. The testing side includes one or more testing reagents that react with the sample to produce a detectable product related to the detection and/or quantity of at least one analyte in the sample.

Usually, the membrane is porous and more usually has a broad range of pore sizes. Thus, after passing through the transfer element or being otherwise transferred, e.g., wicked by capillary forces, etc., blood enters the sample side of the membrane and encounters increasingly smaller pores as it penetrates through the membrane. Eventually, solids such as red blood cells reach a position in the membrane where they cannot penetrate any further. The balance of the sample, still containing dissolved glucose, penetrates through to the testing side. Suitable membrane materials include, but are not limited to, polysulfone, nylon, nitrocellulose, cellulose ester(s), etc.

Sample that has passed through the membrane reacts with the at least one testing reagent, thereby causing a light-absorbing dye to be formed in the void volume near the testing side, which dye substantially affects reflectance from the membrane.

The size of the porous membrane may vary depending on a variety of factors, where such factors include the particular testing reagents used and the like. However, to perform an accurate measurement, the minimum volume required by the reaction area is usually about 0.1 to 5 microliters, usually about 1 to 3 microliters and more usually about 1.5 to 2.5 microliters.

The Transport Element

As described above, the transport element is configured to accept a physiological sample, e.g., whole blood, and transport at least a portion of that sample to the membrane. The transport element is typically configured or sized to extend past one or more ends of the reaction area so as to form a reservoir for holding excess amounts of sample. As described above, in conventional reagent test strips of this type, the entire transport element, including the reservoir areas, generally is capable of holding from about 12 to 230 microliters of blood, usually about 30 to 80 microliters of blood, while the portion or area directly above the reaction area is typically capable of holding from about 5 to 15 microliters of blood, usually from about 6 to 10 microliters of blood and passing from about 1.5 to about 2.5 microliters of blood to the reaction area. As noted above, the fluid transport element may be porous or, in other embodiments, may be non-porous. In those porous embodiments, the fluid transport element may be made of a variety of materials, including natural fibers, such as cotton or paper (i.e., cellulose), as well as polyesters, polyamides, polyethylene and other synthetic polymers. In certain embodiments, the material may be treated with a surfactant. Surfactant treated polyethylene is particularly well suited for use in the subject invention, such as surfactant treated porous polyethylene available from the Porex Corp. of Fairburn, Ga. In those non-porous embodiments of the subject invention, the transport element is made of a non-porous material, and is typically a highly wettable non-porous plastic material, such as an antifog film. Suitable antifog films include 3M 9962 AF polyester film manufactured by 3M Corporation, St. Paul, Minn., or other polymeric films such as polyester, polystyrene, polyolefin, polycarbonate, etc., where suitable wetting agents may be included, such as sorbitan esters of fatty acids, alkyl phenol ethoxyethylene esters of oleic acid, etc.

In many embodiments of the present invention, e.g., those embodiments employing a porous transfer element, the transport element includes at least two areas: a first area and a second area. The first area, positioned substantially over the support structure of the test strip, is configured to, and acts as, a reservoir for holding excess amounts of sample. The second area, positioned substantially over the reaction area of the strip, is configured to transport or transfer at least a portion of a physiological fluid sample to the reaction area of the test strip.

As mentioned above, the test strips of the subject invention are configured or sized to require only a minimal volume of sample in order to perform an accurate test, i.e., the transfer element requires only a minimal sample or void volume in order to pass the requisite sample volume to the reaction area. In other words, typically the second area, which is the area most responsible for transporting sample to the reaction area, e.g., the area which lies substantially above the reaction area, is configured and shaped to only require a minimal sample volume before it becomes saturated and passes a required sample volume to the reaction area. More specifically, the patient need provide less sample in order to saturate the second area, while the second area is still able to transfer the volume of sample needed by the reaction area. For example, the second area is configured and/or shaped to require less than about 4 to 5 microliters of sample before it can pass about 1.5 to 2.5 microliters of sample to the reaction area of the test strip. In certain subject test strips, at least one dimension (shape, size, etc.) of the second area of the transport element differ from at least one dimension of the first area of the transport element, as will now be described in greater detail.

Referring now to the Figures, where like numerals refer to like components or features, FIG. 1A illustrates an exploded view of an exemplary embodiment of the subject device. FIG. 1A shows device 2 having a support layer 4 with aperture 3 therethrough, to which membrane 6, and thus reaction area 8, are associated. Aperture 3 is shown having a rounded configuration, but other shapes are contemplated by this invention as well. In those embodiments where the aperture is of a substantially round shape, i.e., substantially circular, oval, elliptical, and the like, the diameter of the aperture 3 usually ranges from about 0.010 to 0.21 inches, usually from about 0.14 to 0.20 inches and more usually from about 0.15 to 0.19 inches.

Device 2 also includes porous transport element 10, where the porous transport element 10 has at least first areas 12 and a second area 14. The excess sample reservoir areas, i.e., the first areas 12, typically have a pore volume from about 40 to 60%, more usually from about 45% to 55%, but in any case the pore volume usually does not exceed about 55%, nor does the pore volume usually fall below 45%. Area 14 typically has a pore volume from about 20 to 50%, more usually from about 25 to 45%, but in any case the pore volume usually does not exceed about 40%, nor does the pore volume usually fall below about 25%. The size of the pores of the second area 14 typically ranges from about 50 to 200 microns, usually from about 60 to 150 microns and more usually from about 80 to 120 microns. Typically, the total length of the transport element, i.e., the total length of all of the areas, ranges from about 0.5 to 1.5 inches, usually from about 0.8 to 1.2 inches and more usually from about 0.9 to 1.1 inches and the width of the transport element usually ranges from about 0.15 to 0.60 inches usually from about 0.18 to 0.40 inches and more usually from about 0.20 to 0.30 inches.

As described above, in certain embodiments of the subject invention, certain dimensions of the first areas and the second areas differ. In other words, the areas may differ so that each area is configured to optimally provide it's respective function. Each of the first areas 12 of device 2 has a length 16 that ranges from about 0.10 to 0.45 inches, usually from about 0.22 to 0.55 inches and more usually from about 0.30 to 0.45 inches and each has a width 18 that ranges from about 0.16 to 0.600 inches usually from about 0.18 to 0.40 inches and more usually from about 0.20 to 0.3 inches.

A feature of the second area 14 is that it is configured and dimensioned so as to provide optimum sample transport to the reaction. The second area can be a variety of shapes, including, but not limited to, a shape that is substantially rectangular, square, circle, oval, elliptical, diamond, and the like. Where the second area 14 has a substantially rectangular or square shape, such as the embodiment represented by device 2, it typically has a length 20 that ranges from about 0.10 to 0.40 inches, usually from about 0.15 to 0.35 inches and more usually from about 0.20 to 0.30 inches and a width 22 that ranges from about 0.15 to 60 inches usually from about 0.18 to 0.40 inches and more usually from about 0.20 to 0.30 inches. In the embodiments of FIG. 1A having a substantially rectangular second area, typically the portion of the second area substantially directly over the aperture 3 is capable of becoming saturated with a volume of sample in the range from about 1 to 7 microliters, usually from about 3 to 6 microliters and more usually from about 4 to 5 microliters and passing a volume to the reaction area in the range from about 0.1 to 5.0 microliters usually from about 1.0 to 3.0 microliters and more usually from about 1.5 to 2.5 microliters. FIG. 1B shows the configured test strip of FIG. 1A.

In the embodiments having a substantially circular second area, such as the embodiments represented by FIG. 1C, the second area 32 typically has a diameter that ranges from about 0.10 to 0.21 inches usually from about 0.14 to 0.20 inches and more usually from about 0.15 to 0.19 inches. In the embodiments of FIG. 1C having a substantially circular second area, typically the second area is capable becoming saturated with a volume of sample in the range from about 1 to 7 microliters usually from about 3 to 6 microliters and more usually from about 1.5 to 2.5 microliters and passing a volume to the reaction area in the range from about 0.1 to 5.0 microliters usually from about 1.0 to 3.0 microliters and more usually from about 1.5 to 2.5 microliters. FIG. 1D shows the configured test strip of FIG. 1C.

Another feature of the particular embodiments of FIGS. 1A through 1D (and also FIGS. 1E through 1G, as will be described below) is that the first area and the second area of the transport element have differing thicknesses. (However, as mentioned above, the first area and the second area may be of the same thickness.) More specifically in those embodiments where the thicknesses of the areas differ, the thickness of each of the first areas 12 is greater than the thickness of the second area. In other words, the ratio of the thicknesses of each of the first areas to the thickness of the second area, i.e., the thickness of each of the first areas/the thickness of the second area, ranges from about 1.1 to 1.9, typically from about 1.1 to 1.7 and more typically from about 1.2 to 1.5. Accordingly, the thickness of each of the first areas range from about 0.019 to 0.031 inches, usually from about 0.020 to 0.030 inches and more usually from about 0.021 to 0.027 inches, whereas the thickness of the second area ranges from about 0.015 to 0.022 inches, usually from about 0.016 to 0.021 inches and more usually from about 0.017 to 0.020 inches.

FIG. 1E illustrates an exploded view of an exemplary embodiment of the subject test strip having one or more extensions located on the sides of the transport element for passing sample to the transport element and FIG. 1F shows the configured test strip of FIG. 1E. As such, the device 40 of FIG. 1E is substantially the same as the devices of FIGS. 1A through 1D (herein shown with the substantially circular transport element of FIG. 1C, but transport element may be of any suitable shape, as described above), except that the second area 32 of the transport element includes at least two lateral extensions 44 associated with the second area 32, where such lateral extensions are configured to facilitate sample application to the transport element, and more specifically to the second area 32 of the transport element. In certain embodiments where one or more lateral extensions are present, the total length of the porous material, i.e., the lengths of the first areas and the second areas together, may be minimized by minimizing the lengths of the first sections. This particular embodiment includes two lateral extensions, each one positioned on substantially opposing sides of the fluid transport element, but it will be apparent that any number of lateral extensions may be used, for example from 1 to 50 lateral extensions may be used. Regardless of the number of lateral extensions, typically the material from which the lateral extensions are made is the same material as the second area 32, so as to be a unitary piece of construction, i.e., the same piece of material. However, lateral extensions 44 may also be made of a different material than the second element 32. A variety of different materials may be used in the manufacture of the lateral extensions, where the only requirement is that the material enable sample to be wicked or otherwise transported to a second area of the transport element. Where the lateral extensions are the same material as the transport element, i.e., are of a porous material, the lateral extensions typically have a width that ranges from about 0.20 to 0.25 inches, usually from about 0.030 to 0.060 inches and more usually from about 0.45 to 0.55 inches. The length of the lateral extensions generally ranges from about 0.020 to 0.070 inches, usually from about 0.030 to 0.060 inches and more usually from about 0.45 to 0.55 inches. In another embodiment of the subject test strips, lateral extensions 44 are elongated, hollow or tube-like structures, such that the lateral extensions have a fluid transport channel or lumen therethrough (not shown), such that the lateral extensions are capable of transferring sample to the second area of the test strip through the channel and where the channels may be dimensioned so as to exert a capillary force upon a physiological fluid.

FIG. 1G illustrates an exploded view of yet another exemplary embodiment of the present invention. In this particular embodiment, device 50 is substantially the same as device 40 of FIG. 1E except for the configuration of the support layer. The support layer 5 includes aperture 3 as described in the previous embodiments, however the support layer 5 also includes notches 7, which lie substantially adjacent or next to the aperture 3. In this particular embodiment, two notches are shown, however any number of notches may be used, e.g., at least one notch may be formed, two notches may be formed or more notches may be formed in the support layer. As such, membrane 6 and lateral extensions 44 protrude or extend beyond the support layer at the position of the notches. The notches 7 are thus configured to minimize sample contamination to the underside 9 of the support layer 5, where such contamination can result in an automated device such as a meter (not shown), into which the device is inserted for automatically determining the concentration of at least one analyte in the sample, being un-clean and possibly causing incorrect or erroneous meter readings as well. Typically, the length of a notch will range from about 0.010 to 0.020 inches, usually from about 0.15 to 0.040 inches and more usually from about 0.020 to 0.030 inches and the width of a notch, i.e., the distance the notch is cut or relieved into the support layer, will range from about 0.10 to 0.50 inches, usually from about 0.20 to 0.40 inches and more usually from about 0.25 to 0.35 inches.

FIG. 2A illustrates an exploded view of another exemplary embodiment of the subject invention and FIG. 2B shows the configured test strip of FIG. 2A. In this particular embodiment the transport element is non-porous, where such a non-porous transport element is configured to transfer a sample to the reaction area by wicking the sample between the transport element and the membrane, typically by capillary action. Accordingly, the non-porous transport element may lie substantially directly adjacent, i.e., substantially directly above, the membrane or may be spaced apart from the membrane, i.e., the non-porous membrane may be lie a distance above or adjacent the membrane. Thus, the non-porous transport element may lie a distance from about 0 to 0.001 inches above the membrane, usually about 0 to 0.0001 inches above the membrane.

In this embodiment, device 60 has a transport element 62 which is of a nonporous plastic material, such as those suitable materials described above. Usually, each of the first areas 64, the second area 66 and the lateral extensions 68 are all made of the non-porous material. In certain embodiments of the subject devices, the transport element 62, and in particular the lower surface 63 of the transport element 62, includes a means to direct sample, for example, a means to direct sample flow in a regular or predictable manner. Such a means of sample direction may include, but is not limited to, a pattern such as a knurl pattern or one or more protrusions (not shown) positioned on the lower surface 63. Furthermore, the pattern may include one or more protrusions having grooves or channels therein to further assist in directing sample, or any combination of the above.

Although the material from which the transport element is made differs from the material of the transport elements described above, i.e., the transport element is non porous in contrast to the porous transport elements described above, the configuration is substantially the same. In other words, the first areas 64, the second area 66 and the lateral extensions 68 are of substantially the same shape and dimensions of the corresponding features in device 50 of FIG. 1G, except that the first and second areas do not necessarily differ in thickness. Because sample is applied from the side(s) of the strip and the transport element is non-porous, the lengths of the first sections 64 may be minimized, as they do not provide reservoir functions. As such, the thickness of the nonporous transport element 62, i.e, the thickness of all of the areas of the non-porous transport element 62, ranges from about 0.001 to 0.002 inches, usually from about 0.003 to 0.015 inches and more usually from about 0.005 to 0.012 inches. In this particular embodiment, the second area of the transport element is circular, however, other shapes are contemplated by this invention as well, such as a substantially rectangular shape or the like, as represented by the transport element shown in FIG. 2C, where the transport element of 2C shows substantially square or rectangular second area 69 and lateral extensions 71.

Certain embodiments of the subject device may include the presence of a sample confinement element. For example, FIGS. 2A and 2B show device 60 with a sample confinement element 70, where such a confinement element is configured to prevent sample which may have flowed onto the upper or top side of the device 60, i.e., located on the side 72 of sample transport element 62, from contaminating a meter into which the device 60 may be inserted. Usually, sample confinement element 70 has substantially the same length and width as the non-porous transport element to which it is associated, although the sample confinement element may be smaller or larger than the non-porous transport element to which it is associated. Sample confinement element 70 typically includes notches 73, where such notches form area 74 which lies substantially over second area 66 of transport element 62. Sample confinement element 70 is configured to substantially confine or retain sample to an area below or underneath the sample confinement element. Sample confinement element may be made from a variety of materials, with the only provision that the material does not substantially interfere with the reaction of the test strip, i.e., the concentration determination of at least one analyte in a physiological fluid sample applied thereto, where representative materials include, but are not limited to, polyethylene, polypropylene, polyester, polycarbonate, polystyrene, polyamide, etc.

FIG. 3A illustrates an exploded view of another exemplary embodiment of the present invention and FIG. 3B shows the configured test strip of FIG. 3A. In this embodiment, positioned on a first side, i.e., the sample application side, of membrane 6 is a spacer layer 76 having an aperture 77 formed therein, where such an aperture is positioned substantially above the membrane to direct sample thereto. The spacer layer 76 may be fabricated from any convenient material, where representative suitable materials include, but are not limited to polyester, polyethylene, polypropylene, polystyrene, polycarbonate, polyamide, etc., where the surfaces of the spacer layer may be treated so as to be adhesive with respect to their respective adjoining materials or layers, thereby maintaining the structure of the device. Spacer layer 76 is generally configured to provide a capillary transport area 79 between the membrane 6 and the non-porous transport element 78, described below, such that sample is wicked, typically by capillary forces, between the membrane 6 and the non-porous transport element 78. As such, the thickness of the spacer layer 76 generally ranges from about 0.001 to 0.015 inches, usually from about 0.001 to 0.007 inches and more usually from about 0.002 to 0.006 inches. Spacer layer 76 generally has a length that ranges from about 0.3 to 1.5 inches, usually from about 0.5 to 1.2 inches and more usually from about 0.9 to 1.1 inches. The width of the spacer layer 76 typically ranges from about 0.15 to 0.60 inches usually from about 0.18 to 0.40 inches and more usually from about 0.2 to 0.3 inches. Aperture 77, configured to transfer and substantially confine sample to the membrane 6, generally has a diameter in the range from about 0.010 to 0.21 inches usually from about 0.14 to 0.20 inches and more usually from about 0.15 to 0.19 inches.

As mentioned above, device 80 includes a non-porous transport element 78, as mentioned above, and a sample confinement element 70. Accordingly, the non-porous transport element 78 is positioned between the spacer layer 76 and the sample confinement element 70, where the sample confinement element 70 is configured to prevent sample from contaminating a meter, as described above, and the non-porous transport element 78 is configured to form a capillary area between itself and the membrane, through which sample travels to the membrane 6. Typically, the length and width of the non-porous transport element 78 is substantially the same as the length and width of the spacer layer 76. In this particular embodiment, the shape of the non-porous membrane is represented as a solid rectangular structure, however other shapes are suitable as well, such as the shapes of the transport elements of FIGS. 2A through 2C.

Methods of Manufacture

As summarized above, the present invention provides methods of manufacturing reagent test strips. More particularly, the present invention provides methods of manufacturing the fluid transport element of the reagent test strip. By reagent test strip is meant an article of manufacture that includes at least a support material, membrane and fluid transport element. Exemplary reagent test strips that may be produced using the subject methods are described in greater detail above.

Thus, a feature of the subject invention is the transport element which is configured to efficiently transfer a physiological fluid sample to the reaction area of a test strip. In certain embodiments of the subject invention, as described above, the transport element may be a porous transport element and may include various areas or sections, where such various sections may be of different dimensions and/or shapes. For example, the thickness of a first area of a porous transport element may be greater than the thickness of a second area of the transport element (see FIGS. 1A-1G). Suitable materials from which the porous transport element may be made include, but are not limited to, natural fibers, such as cotton or paper (i.e., cellulose), as well as polyesters, polyamides, polyethylene and other synthetic polymers. In certain embodiments, the material may be treated with a surfactant. Surfactant treated polyethylene is particularly well suited for use in the subject invention; for example porous polyethylene available from the Porex Corp. of Fairburn, Ga.

Compression molding is one type of manufacturing process which is particularly suitable for fabricating the porous transport element of the present invention, and more particularly for configuring the porous transport element into a desired shape and/or pattern. An advantage of compression molding is the ability to use the same piece of material to fabricate the various porous transport element areas, i.e., to fabricate the porous transport element as a unitary piece of construction having areas or areas of different dimensions. Furthermore, the ability to customize and precisely detail certain dimensions of the porous transport element consistently is yet another advantage of using compression molding.

Generally in the subject methods, the material of interest to be compressed is positioned between portions of a compression molding assembly and the two portions are brought together under pressure, oftentimes under pressure and heat, to compress or otherwise shape the material therebetween. Typically, the portions of the compression molding assembly are made of a substantially hard and robust material so as to withstand the pressure and/or heat used in the subject methods.

Accordingly, after the provision of the compression molding assembly, a precursor porous transport element is provided. The precursor porous element may be any convenient size, for example it may be sized to provide one porous transport element or it may be sized to provide a plurality of porous transport elements.

The next step in the subject methods following provision of the porous transport element precursor is to place the precursor between two spaced apart portions of the compression molding assembly, where such portions are configured to receive the precursor and form the precursor into a predetermined shape or pattern. Accordingly, the precursor is placed between two portions having alignable surfaces, e.g., a male portion having a protrusion which is a negative image of the desired shape, for example a negative image of a second area of a fluid transport element as described above, and a female portion having a cavity or groove to receive the protrusion of the male portion.

Following positioning of the precursor between the two portions of the assembly, the surfaces of the two tools are brought together. More specifically, the surface of one of the portions is brought into close proximity to, or contact with, the surface of the other portion, with the precursor positioned between the two surfaces such that an area of the precursor associated with the protrusion of the male portion is positioned or pushed into the corresponding female groove and compressed. Typically, the pressure under which the surfaces are brought together is great enough to position and compress the precursor between the male and female portions of the assembly, but not so great as to damage or otherwise adversely effect the precursor. Specifically, the pressure is great enough to compress an area of the precursor, and more specifically to form an area of the precursor associated with a second area of the transport element, as described above, so that the thickness of the formed second area is less than the thickness of the precursor area(s) associated with the first areas of a transport element. For example, the ratio of the thickness of each of the first areas to the thickness of the second area, i.e., the thickness of each of the first areas/the thickness of the second area, ranges from about 1.1 to 1.9, typically from about 1.1 to 1.7 and more typically from about 1.2 to 1.5. Accordingly, the thickness of each of the first areas ranges from about 0.019 to 0.031 inches, usually from about 0.020 to 0.030 inches and more usually from about 0.021 to 0.027 inches, whereas the thickness of the second area ranges from about 0.015 to 0.022 inches, usually from about 0.016 to 0.021 inches and more usually from about 0.017 to 0.020 inches. Sufficient pressure is applied to achieve the desired clearance between the two portions of the compression molding assembly, specifically between the two portions at the substantial center of the second area. Clearance typically ranges from about 0.010 to 0.020 inches, usually from about 0.012 to 0.018 inches, and more usually from about 0.012 to 0.015 inches. Oftentimes, heat is also applied to form the transport element, where such heat may be applied either before or during the pressure application, for example heat may be applied at temperatures ranging from about 40 to 120° C.

Following compression, the compressed transport element is removed from the assembly. In those embodiments where the precursor is sized to provide a plurality of transport elements, the precursor is then cut into a plurality of transport elements.

Referring again to the drawings, FIG. 4A shows an exemplary embodiment of a tool assembly suitable for use in the compression molding of the porous transport element of the present invention. It is to be understood that any convenient mold assembly may be used such as circular or rotary die assemblies and the like. FIG. 4A shows a compression mold assembly 80 having a first element, i.e., a base or female portion 82, where the female portion includes a cavity or groove 84 therein, and a second element, i.e., an alignable male or top portion 86 having a protrusion 88 receivable by the groove 84. The protrusion 88 provides a negative or opposite image of the desired area of the porous transport element to be compressed or shaped, such as the second area of the porous transport element of FIGS. 1A to 1G. Initially, as shown in FIG. 4A, the male and female portions of the tool assembly are spaced apart to receive a precursor transport element. FIG. 4B shows a precursor 100 positioned between the two elements 82 and 86.

FIG. 4C shows a side view of an exemplary transport element that has been formed by the subject methods it an unfolded state, for example transport element 10 of FIG. 1A. Transport element 90 includes first areas 12 and second area 14, where the thickness of the second area is less than the thickness of the first areas due to the compression molding methods described above. FIG. 4D shows a side view of the formed transport element of FIG. 4C, herein shown in its pressed or folded state during or after compression. The molded transport element is then operatively associated with the other components of the test strip in any convenient manner such that in its unfolded state, the transport element, or rather the second section thereof, is configured and positioned substantially directly on top the membrane such that there is not a gap or there is substantially no gap between itself and the underlying membrane, i.e., the element applies a spring force to the underlying membrane such that it rests on or substantially on the membrane and may even apply a spring force to the membrane.

Methods of Use

As summarized above, the subject invention also provides methods for determining the concentration of an analyte in a sample, where the methods advantageously allow for the efficient transfer of sample to the reaction area of the test strip. More specifically, methods are described for applying a fluid sample to a test strip, where such a test strip is used to determine the concentration of at least one analyte in a physiological sample. The subject methods find use in the determination of a variety of different analyte concentrations, where representative analytes include glucose, cholesterol, lactate, alcohol, and the like. In many embodiments, the subject methods are employed to determine the glucose concentration in a physiological sample.

While in principle the subject methods may be used to determine the concentration of an analyte in a variety of different physiological samples, such as urine, tears, saliva, and the like, they are particularly suited for use in determining the concentration of an analyte in interstitial fluid, blood or blood fractions, and more particularly in whole blood.

Generally, a sample of physiological fluid is applied to a reaction area of a test strip, where such a sample may be transported to the reaction area by passing through a transport element or being applied directly to the reaction area. In those embodiments of the subject methods where the sample is transported to the reaction area of the test strip by passing through a transport element, the sample may be applied directly to the transport element or first applied to a portion of the test strip operatively associated with the transport element, which portion then moves or facilitates transport of the sample to the transport element. In those embodiments where the sample is applied directly to the reaction area, sample may be transported by capillary forces to the reaction area. The various methods of physiological fluid application will now be described in more detail.

As described above, sample may be applied directly to the transport element or may be applied first to another portion or structure of the test strip and then moved or otherwise transported to the transport element before at least a portion of the sample is then passed to the reaction area from the transport element. In other words, sample may be applied directly to the top of the transport element or may be fed to the transport element via one or more sides of the transport element, where such side feeding advantageously enables the user to view the transport element, i.e., the transport element is unobstructed by the user's finger or other device containing the sample, such as a capillary tube or the like, where such unobstructed viewing enables visualization of when the transport element is saturated with sample, thereby avoiding over-filling of the transport element which may cause incorrect analyte concentration readings. Accordingly, sample may initially be applied to one or more sides of the test strip, where such sample is then moved or passed to the transport element.

In certain methods, sample is applied to one or more elements operatively associated with the side(s) of the transport element, such as one or more lateral extensions described above, where such elements transfer sample to the transport element, for example by wicking through the sample application element to the transport element. In certain other methods, sample is passed to the transport element through a lumen of the sample application element, typically by capillary forces. Typically, sample in the range from about 1 to 8 microliters is applied to one or more lateral extensions, usually from about 5.5 to 7.5 microliters and more usually from about 6 to 7 microliters.

Sample may also be directly contacted with the reaction area of a test strip. For example, sample may be wicked by capillary forces across the reaction area. In one such embodiment of the subject methods, sample is wicked between the reaction area, or rather the membrane including the reaction area, and a second material layer or structure, such as a non-porous transport element described above (see for example FIGS. 2A-3).

Thus, in one particular embodiment where sample is wicked between the membrane and a second layer, a volume of physiological fluid in the range from about 1 to 4 microliters, usually from about 2.5 to 3.5 microliters and more usually from about 2.5 to 3 microliters is applied between the membrane and a second layer and the physiological fluid sample is then wicked across the membrane by capillary forces formed by the configuration of the membrane and the second layer, and more particularly the lower surface of the second layer. Sample may be wicked in a predictable or regular manner, where such a predictable manner may be accomplished by a sample directing means such as a selected pattern such as a knurl pattern, protrusions, or the like, associated with the second layer, where such patterns, protrusion, etc. assist in directing the flow of sample. Alternatively, an additional layer positioned between the two layers may be used, where such an additional layer has an aperture therein to direct the flow of sample. (see for example FIG. 3).

Regardless of whether sample is directed in a regular manner or not, sample may be applied between the aforementioned membrane and second layers by introducing the sample from the side of the test strip. For example, the second layer may include lateral extensions (see for example FIGS. 2A-2B). As such, sample may be introduced to the lateral extensions and sample may then be moved or transported from the elements to the area between the second layer and the membrane so that it may be wicked by capillary forces across the membrane.

Kits

Also provided by the subject invention are kits for use in practicing the subject methods. The kits of the subject invention include at least one subject test strip, where such test strips include a fluid transfer element, typically porous, for transferring sample to a reaction area of the test strip, where the fluid transfer element may be porous and include a first area and a second area of different thickness and/or the transport element may be non-porous. Oftentimes, the kits of the subject invention include a plurality of such test strips. The kits may also include a reusable or disposable lancing element for accessing and/or collecting the sample from the skin. Furthermore, the kit may also include a reusable or disposable meter that may be used with the subject test strips. Certain kits may include various types of test strips, e.g., where various test strips contain the same or different reagents, e.g., electrochemical and/or calorimetric test strips. Finally, the kits may further include instructions for using the subject devices for determining the concentration of at least one analyte in a physiological sample. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides a simple, quick and convenient way to obtain a physiological sample and determine an analyte concentration thereof. The above described invention provides a number of advantages, including ease of use, efficiency and minimal pain. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A test strip for determining the concentration of at least one analyte in a physiological sample, said test strip comprising;
   a support;
   a membrane comprising at least one testing reagent for determining the concentration of at least one analyte in a physiological sample, said membrane having a first surface attached to said support and a second surface opposite said first surface; and
   a fluid transfer element for transferring said sample to said membrane, said fluid transfer element comprising at least a first area and a second area, wherein the thickness of said first area is greater than the thickness of said second area and said second area directly overlies said second surface of said membrane.

2. The test strip according to claim 1, wherein the ratio of the thickness of the first area to the second area ranges from about 1.1 to 1.9.

3. The test strip according to claim 1, wherein said ratio ranges from about 1.1 to 1.7.

4. The test strip according to claim 1, wherein said thickness of said second area ranges from about 0.015 inches to 0.022 inches.

5. The test strip according to claim 1, wherein said fluid transport element comprises a porous material.

6. The test strip according to claim 1, wherein said fluid transport element is selected from the group consisting of cotton, cellulose, polyester, polyamide and polyethylene.

7. The test strip according to claim 1, wherein said fluid transport element comprises a surfactant.

8. The test strip according to claim 1, wherein said second area is substantially rectangular.

9. The test strip according to claim 8, wherein said second area has a length in the range from about 0.10 inches to 0.40 inches and a width in the range from about 0.15 inches to 0.60 inches.

10. The test strip according to claim 1, wherein said second area is substantially circular.

11. The test strip according to claim 9, wherein said second area has a diameter in the range from about 0.01 inches to 0.21 inches.

12. The test strip according to claim 1, wherein said second area is capable of being saturated with a sample volume from about 1 to 7 microliters.

13. The test strip according to claim 1, wherein said second area is capable of transferring a sample volume from about 0.1 to 5.0 microliters to a reaction area of said test strip.

14. The test strip according to claim 1, wherein said second area further comprises at least one lateral extension.

15. The test strip according to claim 14, wherein said at least one lateral extension comprises a lumen therethrough.

16. The test strip according to claim 14, wherein said support layer comprises at least one notch therein, and said at least one lateral extension is configured to extend beyond said at least one notch.

17. A kit for determining the concentration of at least one analyte in a physiological sample, said kit comprising:

(a) at least one test strip according to claim 1; and (b) a substrate comprising instruction for using said at least one test strip to determine said concentration of at least one analyte in a physiological sample.

* * * * *